United States Patent
Tasz et al.

(10) Patent No.: US 8,662,409 B2
(45) Date of Patent: Mar. 4, 2014

(54) MULTI-LAYERED ACTIVE INGREDIENT DISPENSER

(75) Inventors: Maciej K. Tasz, Racine, WI (US); Amelia H. Majerowski, Kenosha, WI (US); Christopher S. Hoppe, Milwaukee, WI (US)

(73) Assignee: S.C. Johnson & Son, Inc., Racine, WI (US)

(*) Notice: Subject to any disclaimer, the term of this patent is extended or adjusted under 35 U.S.C. 154(b) by 465 days.

(21) Appl. No.: 12/898,459

(22) Filed: Oct. 5, 2010

(65) Prior Publication Data

US 2011/0095096 A1 Apr. 28, 2011

Related U.S. Application Data

(60) Provisional application No. 61/254,844, filed on Oct. 26, 2009.

(51) Int. Cl.
*A61L 9/04* (2006.01)
*A24F 25/00* (2006.01)
*A62C 31/00* (2006.01)

(52) U.S. Cl.
USPC ........ 239/6; 239/34; 239/44; 239/45; 239/47; 239/55; 239/303

(58) Field of Classification Search
USPC ......... 239/6, 34, 44, 45, 47, 50, 55, 303, 309, 239/310, 398
See application file for complete search history.

(56) References Cited

U.S. PATENT DOCUMENTS

| | | | |
|---|---|---|---|
| 4,056,612 A | | 11/1977 | Lin |
| 4,534,509 A | * | 8/1985 | Holzner .................... 239/34 |
| 4,874,129 A | | 10/1989 | DiSapio et al. |
| 5,060,858 A | | 10/1991 | Santini |
| 5,497,942 A | * | 3/1996 | Zingle et al. ................ 239/6 |
| 5,556,030 A | | 9/1996 | Paul |
| 5,679,334 A | | 10/1997 | Semoff et al. |
| 5,750,498 A | | 5/1998 | Soeda et al. |
| 5,840,257 A | * | 11/1998 | Bureau et al. ............... 422/125 |
| 6,039,266 A | | 3/2000 | Santini |
| 6,071,506 A | | 6/2000 | Semoff et al. |
| 6,171,560 B1 | | 1/2001 | Pesu et al. |
| 6,177,069 B1 | | 1/2001 | Yokoyama et al. |
| 6,234,455 B1 | | 5/2001 | Wittek |
| 6,335,075 B1 | | 1/2002 | Seto et al. |
| 6,622,890 B2 | * | 9/2003 | Gueret ....................... 222/1 |

(Continued)

FOREIGN PATENT DOCUMENTS

| | | |
|---|---|---|
| EP | 0596212 A2 | 11/1994 |
| EP | 1632251 A1 | 3/2006 |

(Continued)

*Primary Examiner* — Ryan Reis

(57) ABSTRACT

A dispensing device includes a container having a wall that defines an opening into an interior, a first layer of carrier disposed in the interior distal from the opening, and a second layer of carrier disposed between the first layer and the opening, wherein the first layer of carrier isolates the second layer of carrier from the opening. The first layer of carrier has a first characteristic of an active ingredient, and the second layer of carrier has a second characteristic of active ingredient, wherein the first characteristic is different from the second characteristic. A barrier is disposed between the first layer and the second layer to retard or prevent diffusion of the active ingredient of the second layer into the first layer.

17 Claims, 2 Drawing Sheets

(56) References Cited

U.S. PATENT DOCUMENTS

| | | |
|---|---|---|
| 7,172,065 B2 | 2/2007 | Prater |
| 7,344,123 B2 | 3/2008 | Pankhurst et al. |
| 7,350,720 B2* | 4/2008 | Jaworski et al. ............ 239/55 |
| 7,530,503 B2* | 5/2009 | Caserta et al. .............. 239/57 |
| 2003/0091466 A1* | 5/2003 | Benko et al. ................. 422/5 |
| 2004/0094635 A1 | 5/2004 | Harris et al. |
| 2007/0023539 A1* | 2/2007 | Brown et al. ................ 239/34 |
| 2011/0072711 A1* | 3/2011 | Black et al. ................ 43/123 |

FOREIGN PATENT DOCUMENTS

| | | |
|---|---|---|
| JP | 6154545 | 6/1994 |
| WO | WO2005/077427 A2 | 8/2005 |
| WO | WO2009/098693 A2 | 8/2009 |

* cited by examiner

MULTI-LAYERED ACTIVE INGREDIENT DISPENSER

CROSS REFERENCE TO RELATED APPLICATIONS

This application claims the benefit of U.S. Provisional Patent Application No. 61/254,844, filed Oct. 26, 2009, which is hereby incorporated by reference.

FIELD OF THE DISCLOSURE

The present disclosure relates to a device for dispensing one or more active ingredients, such as volatile actives, into the air in a selected location.

BACKGROUND

Devices that dispense active ingredients into the air, such as volatile actives, are used for many reasons, including dispensing fragrances, insecticides, deodorants, and many other types of chemicals (hereinafter, collectively referred to as "actives" or "active ingredients") that are intended to have some desired effect when present in the ambient air of a space such as a room indoors or an outdoor space.

Some such dispensing devices are called passive dispensers in that the device does not include any apparatus that requires some form of energy, often electricity, to dispense the active. Passive dispensers often have some form of carrier, such as a gel or liquid, that has been impregnated or otherwise carries the active, and the carrier and active are contained within an enclosed container. When it is desired to dispense the active, the container is somehow opened, such as by removing an impermeable membrane covering an opening into the container, so that the carrier is in communication with the atmosphere surrounding the device, which thereby allows the active to volatilize from the carrier into the air and disperse passively into the surrounding atmosphere.

Other dispensing devices are called active dispensers in that the device includes an apparatus that requires some form of energy, such as electricity, to activate the apparatus so as to actively assist in dispensing the active into the surrounding atmosphere. Active dispensing devices include devices with heating elements for heating the carrier and devices with fans for blowing air across or from the carrier into the surrounding atmosphere. In general, the purpose of an active dispenser is to speed up the rate at which the active is dispersed into the surrounding atmosphere over passive dispensers so that the desired effect of the active is achieved in a shorter period of time from the time of initial activation of the dispensing device.

One particularly common form of carrier used in both passive and active dispensing devices is a gel, wherein one or more active ingredients, such as fragrance and/or insecticide, is mixed with at least one or more gellant agents in an aqueous solution while in a liquid phase and allowed to transition into a semi-solid gel phase at normal ranges of room temperature, such as generally between 50° F. (10° C.) and 100° F. (38° C.). When the gel is closed within an enclosed container, the gel and the active ingredient are maintained in a relatively stable form. When the container is opened to the surrounding atmosphere, the active ingredient(s) are able to volatilize into the surrounding atmosphere, and the water in the gel also slowly evaporates. At the end of the useful life of the dispenser, the volume of the gel is usually substantially diminished because of the evaporation of the water from the gel, and the active ingredients are substantially completely dispersed from the gel. Basic examples of such dispensing devices are disclosed, for example, in U.S. Pat. No. 2,949,710 to Wheeler, U.S. Pat. No. 6,171,560 to Pesu et al., and U.S. Patent Application Publication No. 2004/0094635 of Harris et al.

In many passive dispensers, the noticeable effect of the active ingredient has a high initial spike that subsequently quickly decreases with time to a much lower noticeable effect in a generally L-shaped curve. This rapid decrease in noticeable effect may be caused by many factors, including an actual decrease in the amount of active ingredient that is dispersed with time, i.e., rate of dispersal or diffusion. Another reason for the decrease in noticeable effect, especially dispensers that dispense fragrances, may be attributed to desensitization or habituation of a person's olfactory senses to the fragrance, which causes the person to notice the initial fragrance quite strongly, but over time, even if the level of fragrance remains constant, the person becomes habituated or desensitized to the fragrance such that the person does not seem to notice the fragrance as strongly as when the person was initially exposed to the fragrance.

The present disclosers have identified that it would be desirable to improve a dispensing device for a volatile active in such a manner that the noticeable effect of the active ingredient does not diminish as rapidly or at all over the useable life span of the dispensing device so that the noticeable effect remains more strongly noticeable in the surrounding atmosphere for a longer period of time.

SUMMARY

According to one aspect, a dispensing device for dispensing an active ingredient includes a container having a wall that defines an opening into an interior. A first carrier is disposed in the interior, wherein the first carrier has a first characteristic of an active ingredient. A second carrier is disposed in the interior, adjacent the first carrier, wherein the second carrier has a second characteristic of an active ingredient. The second carrier completely isolates the first carrier from the opening. A barrier is disposed between the first carrier and the second carrier, wherein the barrier impedes diffusion of the active ingredient of the first carrier into the second carrier.

According to another aspect, a dispensing device for dispensing an active ingredient includes a first container cell having a first face that defines an opening into an interior of the first container cell, and a second container cell having a second face that defines an opening into the interior of the second container cell. The first face is matingly complementary to the second face. A first carrier is disposed in the interior of the first container cell, and a second carrier is disposed in the interior of the second container cell. The first carrier has a first characteristic of an active ingredient, and the second carrier has a second characteristic of an active ingredient. A hinge that connects the first container cell to the second container cell, and the first and second container cells articulate about the hinge to mate the first face with the second face.

In a further aspect, a method of dispensing an active ingredient from a container is presented. The container has a wall that defines an opening into an interior, wherein a first carrier of a first active ingredient and a second carrier of a second active ingredient are disposed within the interior, and wherein the second carrier isolates the first carrier from an exterior of the container. The method comprises the step of allowing the second active ingredient to disperse through the opening into the exterior of the container. The method also includes the step of allowing the first active ingredient to disperse through the second carrier and through the opening into the exterior of the container.

Other aspects and advantages of the present disclosure will become apparent upon consideration of the following detailed description, wherein similar structures have similar reference numbers.

DETAILED DESCRIPTION

Figure 1:
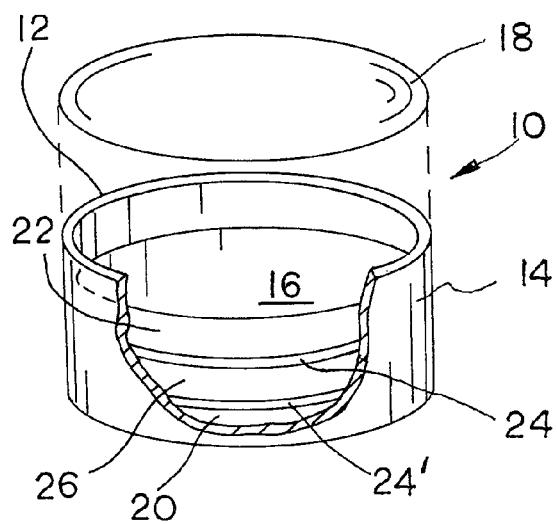
FIG. 1 is a partial cutaway isometric view of a volatile active dispensing device.

Disclosed herein is a dispensing device and method of dispensing an active ingredient, such as a volatile active, from a carrier in such a manner that, in at least some forms, helps maintain the noticeable effect of the active ingredient at a more consistent level for a longer time than prior dispensing devices.

In one form, a dispensing device includes a container having a wall that defines an opening into an interior. A first layer of carrier is disposed in the interior distal from the opening, and a second layer of carrier is disposed between the first layer and the opening, wherein the second layer of carrier isolates the first layer of carrier from the opening. The first layer of carrier has a first characteristic of an active ingredient, and the second layer of carrier has a second characteristic of active ingredient, wherein the first characteristic is different from the second characteristic. A barrier is disposed between the first layer and the second layer to retard or prevent diffusion of the active ingredient of the second layer into the first layer.

The second layer may completely surround and envelop the first layer, or the first and second layers may be horizontal. Further, more than two layers of carriers may be incorporated into the dispensing device, wherein adjacent layers have active ingredients with different characteristics, and the layers may be horizontal, vertical, or mixed horizontal and vertical.

The first and second carriers may be gels, liquids, and/or permeable solids. In some forms, one of the first and second layers may be a gel, and the other of the first and second layers may be a liquid. In other forms, one of the first and second layers may be a gel, and the other of the first and second layers may be a porous solid.

Further, the first characteristic may include an active ingredient of a first type, and the second characteristic may include an active ingredient of a second type, and/or the first characteristic may include a first fragrance, and the second characteristic may include a second fragrance. In some forms the first characteristic may include a first concentration of active ingredient, and the second characteristic may include a second concentration of the same active ingredient. The first concentration may be approximately three percent, and the second concentration may be approximately nine percent, and the first concentration and the second concentration may be selected such that the average concentration over a useful life span of the dispensing device is a preselected concentration between the first concentration and the second concentration, wherein the average concentration may be approximately six percent.

The barrier may be removable, such as a membrane that may separate the first layer from the second layer, wherein the membrane may be impermeable to the active ingredient(s) and may completely separate the first layer from the second layer. The impermeable membrane may be a film that is removable from between the first layer and the second layer. In some forms, the impermeable membrane may be a sheet that may be pulled out from between the first layer and the second layer without disturbing the layers, and the impermeable membrane may include a tab portion that is exposed on an exterior of the container. The impermeable membrane may be a foil, and/or the impermeable membrane may be thermoplastic. In additional forms, the barrier may include a third layer of a carrier disposed between the first layer and the second layer, wherein the third layer isolates the first characteristic from the second characteristic, and wherein the third layer may not have an active ingredient mixed therein.

The first layer may be disposed in a first container cell and the second layer may be disposed in a second container cell spaced from the first container cell, wherein an opening in the first container cell may be sealingly mated to an opening in the second container cell to form the container, and one or more impermeable barriers covering the openings into the first and second container cells are removed when the first and second container cells are mated together. A second opening in one of the container cells is also covered by a removable impermeable barrier, such that the second opening may be uncovered at least when or after the first container cell is mated to the second container cell. A hinge member may connect the first and second container cells, wherein the first and second container cells may be articulated about the hinge member to mate together.

Turning now to the drawings, as shown in FIG. 1, a dispensing device 10 includes a container 12 having a wall 14 that defines an opening 16 into an interior. A cover 18, such as a lid or film membrane that is impermeable to volatile actives, preferably covers the opening 16 and thereby completely encloses the interior of the container 12. A first layer 20 of a carrier is disposed in the interior of the container distal from the opening 16, and a second layer 22 of a carrier is disposed between the first layer 20 and the opening 16, wherein the second layer 22 isolates the first layer 20 from the opening 16. The carrier of the first layer 20 carries an active ingredient having a first characteristic, and the carrier of the second layer 22 carries an active ingredient having a second characteristic, wherein the first characteristic is different from the second characteristic. Additional layers of carriers may be incorporated into the diffusion device 10 in a similar manner, wherein adjacent layers carry active ingredients with different noticeable characteristics, as discussed further herein.

Preferably, the carriers of the first and second layers 20, 22 are gels, such as are readily known to those skilled in the art of air fragrancing and delivery of volatile actives. Some non-limiting examples of gels that are usable with the dispensing device include carrageenan and/or guar-based gels, such as disclosed in U.S. Pat. No. 2,927,055 to Lanzet, U.S. Pat. No. 5,741,482 to Modi, and WO 98/19717 by Modi. Other gels may include polyacrylate-based gels, such as disclosed in U.S. Pat. No. 7,138,367 to Hurry et al. Other gels that are sufficient for slowly releasing active ingredients into the surrounding atmosphere may also or alternatively be used. The carriers may also or alternatively include liquids, such as aqueous or oil based liquids. In the case of using liquid carriers, it is preferable to somehow maintain the carriers in distinct and separate sections, such as with a membrane that is impermeable to the liquid but permeable to the active ingredients, or by using liquids of different density, such as oil and water, so as to prevent intermixing of adjacent carriers. The carriers may also or alternatively include solid carrier matrices, such as porous solid materials and sponges. Additionally, combinations of different types of carriers within a single dispensing device are also contemplated.

The characteristics of the active ingredients carried by the carrier(s) may differ in various ways, but in all aspects, the purpose of having the differing characteristics of the active ingredients in the various layers of the carriers is to diminish the effects of habituation and/or slow the rate of decrease in the dispersion rate of the active ingredient to produce a more steady change in dispersion rate with time. In one aspect, the first active ingredient is different from the second active ingredient. For example and without limitation to these specific examples, if the active ingredients are both fragrances, the first active ingredient may be a first fragrance, such as lilacs, and the second active ingredient may be a second fragrance, such as vanilla. In this manner, when the cover 18 is initially removed from the opening 16, the second fragrance is very strongly dispersed into the surrounding atmosphere and thereby is most strongly perceptible. As the second active ingredient is dispersed from the carrier and its noticeable effect diminishes with time, the first active ingredient will become more prevalent and its noticeable effect increases and may eventually overtake the noticeable effect of the second active ingredient. In another aspect, the second active ingredient may be one type of active, such as a fragrance, and the first active ingredient may be another type of active, such as an insecticide or an odor eliminator. In a further aspect, the first and second active ingredients may be the same active ingredient, such as a single fragrance or a single insecticide, wherein the first characteristic is that the fragrance in the first layer 20 of carrier has a first concentration, such as between six percent and twelve percent, and the second characteristic is that the fragrance in the second layer 22 of carrier has a second concentration, such as more than zero percent and less than six percent. In one preferred embodiment, the average of the concentrations of the active ingredient in the first layer 20 and the second layer 22 averages to a third average concentration over the useful life span of the dispensing device 10. For example, the average concentration of active ingredient over the useful life span of the dispensing device 10 may be a preselected or target value, such as six percent, wherein the first layer 20 has a first concentration of the active ingredient, for example of nine percent, and the second layer 22 may have a second concentration of the active ingredient, for example of three percent, that average over time to an average concentration of about six percent.

In order to retard or prevent diffusion of the active ingredient of the first layer 20 into the second layer 22 before the diffusion device 10 is activated, at least one barrier is preferably disposed between the first layer 20 and the second layer 22. The barrier may be permeable or impermeable. The barrier may also be removable or non-removable. The barrier preferably completely separates the first layer 20 of carrier from the second layer 22 of carrier. In one aspect, the barrier is a film of impermeable material that does not allow the active ingredients to pass therethrough. As shown in FIG. 1, for example, an impermeable barrier 24, such as a sheet of foil or impermeable thermoplastic, is disposed between and completely separates the first and second layers 20, 22 of the carriers. The impermeable barrier 24 is preferably, although not necessarily, at least partly removable from between the first and second layers 20, 22 when the dispersion device 10 is initially activated in such a manner that the active ingredient in the first layer 20 may diffuse into the second layer 22 and thereby begin migrating toward diffusion into the surrounding atmosphere. For example, the impermeable barrier 24 may be completely removed from between the first and second layers 20, 22 or the impermeable barrier 24 may be only partly removed so as to provide only a limited area of fluid communication between the first layer 20 and the second layer 22. If the impermeable barrier 24 is not removable from between the first and second layers 20, 22, the impermeable barrier 24 may be removed after the second layer 20 of carrier has completely evaporated so as to allow diffusion of the first active ingredient from the first layer 20 into the surrounding atmosphere only after the second layer 22 is removed. Other materials can also be used for the impermeable barrier 24. In another aspect, the barrier may include a third layer 26 of carrier that separates the first layer 20 from the second layer 22. In this aspect, the third layer 26 preferably is not impregnated with any active ingredient, and the third layer 26 acts to retard diffusion of the active ingredient in the first layer 20 into the second layer 22. As shown illustratively in FIG. 1, barriers of different types, such as one or more impermeable barriers 24 and 24' and permeable barriers 26, may be combined between adjacent layers 20, 22 of carriers that carry an active ingredient. Preferably, however, only a single type of barrier is disposed between adjacent layers of carriers carrying active ingredients. In addition, the diffusion device 10 may have more than two layers of carriers that carry active ingredients. Each of the layers may be arranged horizontally, stacked in successive layers, and completely separated from the adjacent layers (as shown in FIG. 1). Alternatively, some layers may be arranged vertically (not shown), such as having two or more vertical layers disposed below a top layer that separates the vertical layers from the opening, wherein each vertical layer abuts the top layer.

Figure 2:
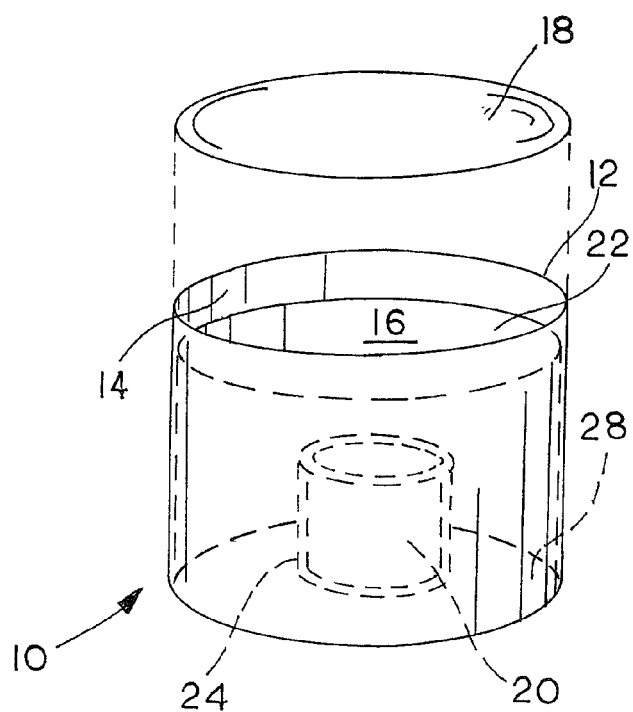
FIG. 2 is an isometric view of another volatile active dispensing device with hidden features shown in broken lines.

Turning now to FIG. 2, another arrangement of layers in the dispensing device 10 is shown, wherein the first layer 20 of carrier is completely encased within or surrounded by the second layer 22 of carrier on at least a top and all sides of the first layer 20. The first layer 20 may take any desired shape and is not limited to the shape shown. The first layer 20 may rest directly on a bottom wall 28 of the container 12, or the second layer 22 may completely envelope all sides of the first layer 20 such that all outer surfaces of the first layer 20 directly engage the second layer 22. One or more barriers as disclosed previously herein may be disposed between the first layer 20 and the second layer 22 to prevent or retard diffusion of active ingredient in either layer 20 or 22 to the other layer.

Figure 3:
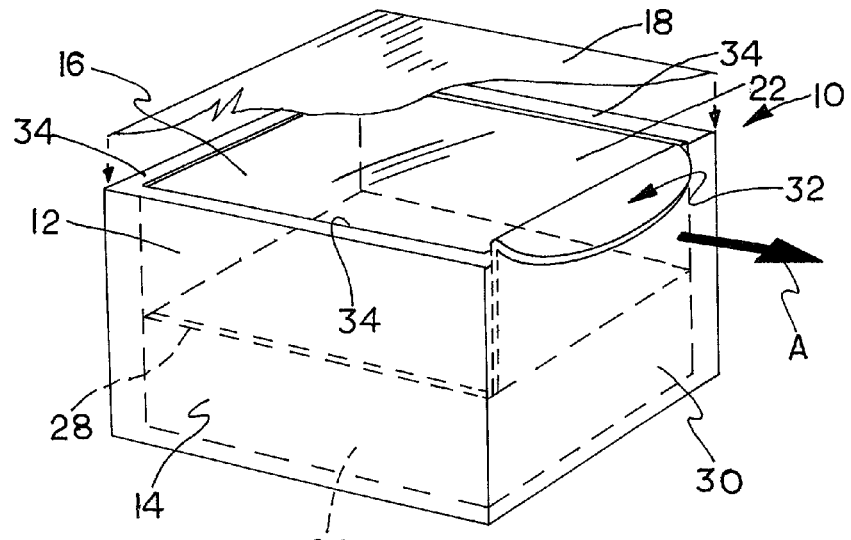
FIG. 3 is an isometric view of a further volatile active dispensing device with hidden features shown in broken lines.

In FIG. 3, another arrangement of a dispensing device 10' is shown in which the barrier is completely removable between the first layer 20 of carrier and the second layer 22 of carrier. Similar to the dispensing device 10 shown in FIG. 1, the container 12 has a wall 14 that defines an opening 16 into the interior of the container 12. In this arrangement, the wall 14 defines a generally rectangular box and the opening is defined by an open top side of the box. The cover 18 (shown in partial cutaway for clarity) is preferably an impermeable film that is removably held onto a top edge of the opening 16 by an adhesive or a lid that sealingly engages around the top edge of the opening 16. When the cover 18 is removed from the container 12, a top surface of the second layer 22 of carrier is exposed to the surrounding atmosphere. The first layer 20 includes an active ingredient having a first characteristic, such as a first fragrance. The first layer 20 is disposed at the bottom of the interior distal from the opening 16 (as seen in FIG. 3). The second layer 22 is disposed over the first layer 20 below the opening 16 and completely covers the first layer 20, thereby isolating the first layer 20 from the opening 16. The opening 16 is preferably the only opening into the interior of the container 12. A barrier film 28 is disposed between and completely separates the first layer 20 and the second layer 22 such that the active ingredients cannot disseminate between the first layer 20 and the second layer 22. The barrier film 28 is flexible and impermeable and includes a portion that extends up the side of the second layer 22 along an inner surface of one side 30 of the container 12 and projects out of the opening adjacent the side 30 to form an exposed tab member 32. Because the container 12 is generally rectangular and the barrier film 28 is flexible, a user can remove the barrier film 28 from between the first layer 20 and the second layer 22 by pulling on the tab member 32 in the direction shown by arrow A, which causes the barrier film 28 to slide out from between the first and second layers 20, 22, up the inner surface of the side 30, and out of the container 12 through the opening 16. Containment members 34 for preventing the barrier film 28 from also accidentally pulling the second layer 22 of carrier out of the opening 16 when sliding the barrier film 28 out of the container 12 may include an in-turned peripheral lip projecting inwardly from the sidewalls partly over the opening and extending around the opening 16 at or near the top side of the container 12.

Figure 4A:
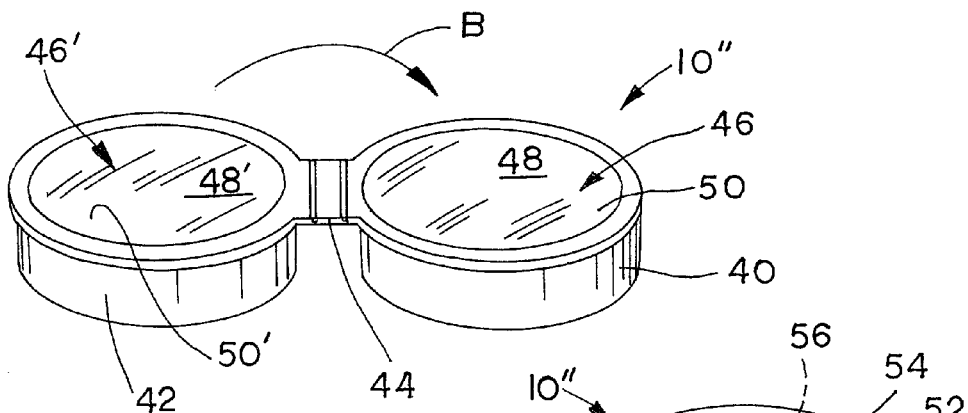
FIGS. 4A and 4B are isometric views of still a further volatile active dispensing device.
Figure 4B:
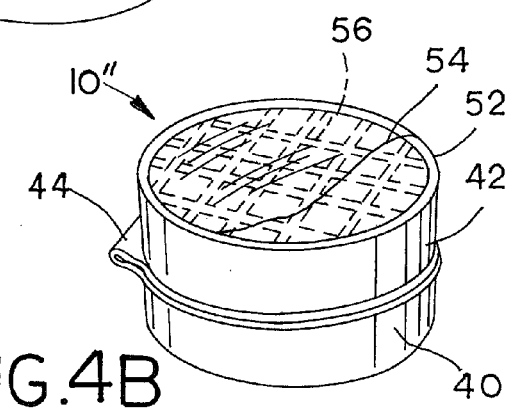

Turning now to FIGS. 4A and 4B, a further arrangement of a dispensing device 10" includes a first container cell 40 and a second container cell 42 hingedly connected by a hinge member 44. Each container cell 40, 42 contains a carrier that carries an active ingredient, such as preferably a gel as described previously that carries a volatile active. The active ingredient in the first container cell 40 has a different characteristic than the active ingredient in the second container cell 42 in any manner as described previously herein, such as having a first fragrance in the first container cell 40 and a second fragrance in the second container cell 42. The dispensing device 10" can be transformed from an inactivated state suitable for storage, as shown in FIG. 4A, to an activated state suitable for dispensing the active ingredient(s), as shown in FIG. 4B. In the inactivated state, the first container cell 40 is separated from the second container cell 42. Each of the first and second container cells 40, 42 includes a top face 46, 46' (as seen in FIG. 4A), wherein the top face 46 of the first container cell 40 is matingly complementary to the top face 46' of the second container cell 42. Further in the inactivated state, the top face 46, 46' of each container cell 40, 42 defines an opening 48 or 48' into an interior of the container cell in which the carrier is located, and a removable impermeable barrier 50 or 50', such as an impermeable film or cap, sealingly covers the opening, and the second container cell 42 includes at least one other dispersion opening 52, such as through a bottom side opposite the top face 46', that is also sealingly covered by another removable impermeable barrier 54 (shown in partial cutaway). To transform the dispensing device 10" from the inactivated state to the activated state, the impermeable barriers 50, 50', and 54 are removed from the respective openings 48, 48', and 52, and the top faces 46, 46' of the first and second cells 40, 42 are mated together as shown in FIG. 4B by articulating the first and second cells 40, 42 about the hinge member 40 in the direction shown by arrow B in FIG. 4A. Preferably, the impermeable barriers 50 and 50' are removed before the top faces 46, 46' of the first and second cells are mated together, but in some embodiments wherein a flexible film barrier is used it may also possible to remove the impermeable barriers 50, 50' after the top faces 46, 46' of the first and second cells 40, 42 are mated together. In either case, the dispensing device 10" is not fully activated until the impermeable member 54 covering the other dispersion opening 52 is also removed so that the active ingredient(s) may disperse into the surrounding atmosphere from inside the now-mated together container cells 40, 42 through the opening 52. Preferably, the dispensing device 10" includes some form of sealing mechanism to maintain the first and second container cells in a sealed and mated state, such as a pressure sensitive adhesive disposed on mating surfaces of the first and second container cells 40, 42 or some other locking mechanism.

Preferably, although not necessarily, when the carrier for the active ingredient(s) comprises a gel, a support structure for the gel is located near an emanating surface of the gel adjacent the opening to provide a support for the gel. One exemplary support structure includes a grid 56 as shown in FIG. 4B disposed just beneath the emanating surface of the gel below the opening 52. Other types of support structures could also be used, such as perforated plate and/or a peripheral collar around the inside surface of the container cell 42 surrounding the opening 52. Some non-limiting examples of such support structures are discussed in Santini U.S. Pat. No. 6,039,266. Further, such a support structure may be incorporated into any of the dispensing devices 10 and 10' and other forms of a dispensing device in accordance with the principles of this disclosure.

The diffusion devices 10, 10', and 10" may be made in a manner known or readily ascertainable to one skilled in the art. In one method for example, if the first and second layers 20 are 22 are formed of gel carriers, a gel infused with a volatile active is deposited into the bottom of the container 12 in liquid phase and allowed to cool into gel phase, the impermeable barrier 26 is placed on top of the cooled first layer 20, and the second layer 22 is then deposited on top of the impermeable barrier 26. The cover 18 is then sealed over the opening 16 to seal the interior of the container 12. In another exemplary example, the first layer 20 and the second layer 22 are pre-formed and subsequently deposited into the container 12 with the barrier inserted therebetween.

The container may be made of any material suitable for containing the carriers and the active ingredient(s), such as metal, thermoplastic, glass.

The description and specific examples of the dispensing devices disclosed herein are illustrative only and are presented for the purpose of enabling those skilled in the art to make and use the technological advance and to teach the best mode of carrying out same. Numerous modifications to the specific examples described herein are anticipated without departing from the spirit of the overall technological advance embodied therein. The exclusive right to all patentable modifications supported by the examples disclosed and described herein is expressly reserved. All patents, patent publications and applications, and other references cited herein are incorporated by reference herein in their entirety.

We claim:

1. A dispensing device for dispensing an active ingredient comprising:
a first container cell having a first face with a first peripheral edge that defines an opening into an interior of the first container cell;
a second container cell having a second face with a second peripheral edge that defines an opening into the interior of the second container cell, wherein the first and second peripheral edges are the same size;
a first carrier disposed in the interior of the first container cell, wherein the first carrier has a first characteristic of an active ingredient;
a second carrier disposed in the interior of the second container cell, wherein the second carrier has a second characteristic of an active ingredient; and a hinge that connects the first container cell to the second container cell, wherein the first and second container cells articulate about the hinge to sealingly attach the first face to the second face.

2. The dispensing device of claim 1, wherein one or more impermeable barriers cover the first and second faces.

3. The dispensing device of claim 2, wherein the impermeable barrier is removable.

4. The dispensing device of claim 3, wherein the second container cell further includes a dispersion opening spaced from the second face, and wherein a removable impermeable barrier covers the dispersion opening.

5. The dispensing device of claim 4, further including a support structure disposed within the second carrier to provide support to the second carrier.

6. The dispensing device of claim 5, wherein the support structure is selected from the group consisting of: a grid, a perforated plate, and a peripheral collar.

7. A method of dispensing an active ingredient from a dispensing device having a first container cell having a closed bottom and a first face that defines a first opening opposite the closed bottom, a second container cell having second and third opposing faces that define a second opening and a dispersion opening, respectively, and a hinge disposed between the first and second container cells, the method comprising the steps of:
    rotating at least one of the first and second container cells about the hinge;
    attaching the first face of the first container cell and the second face of the second container cell;
    allowing a second active ingredient in the second container cell to disperse through the dispersion opening; and
    allowing a first active ingredient in the closed bottom of the first container cell to disperse through the dispersion opening after the second active ingredient has been dispersed.

8. The method of claim 7, further including the step of removing impermeable barriers disposed on the first and second faces and which cover the first and second openings prior to attaching the first face of the first container cell and the second face of the second container cell.

9. The method of claim 8, further including the step of removing an impermeable barrier disposed on the third face over the dispersion opening prior to allowing the second active ingredient to disperse through the dispersion opening.

10. The method of claim 7, wherein the step of attaching the first face of the first container cell and the second face of the second container cell includes activating a pressure sensitive adhesive to attach the first and second faces.

11. The method of claim 7, wherein the first and second faces are attached by a locking mechanism.

12. A dispensing device for dispensing an active ingredient comprising:
    a first container cell having a closed bottom and a first face that defines a first opening opposite the closed bottom;
    a second container cell having a second face that defines a second opening into an interior of the second container cell and a third face opposite the second face and which defines a dispersion opening;
    a first carrier disposed in the closed bottom of the first container cell, wherein the first carrier has a first characteristic of an active ingredient;
    a second carrier disposed in the interior of the second container cell, wherein the second carrier has a second characteristic of an active ingredient; and
    a hinge that connects the first container cell to the second container cell, wherein the first and second container cells articulate about the hinge to mate the first face with the second face such that the third face and the closed bottom face outwardly.

13. The dispensing device of claim 12, wherein an impermeable barrier covers at least one of the first and second faces.

14. The dispensing device of claim 13, wherein the impermeable barrier is removable.

15. The dispensing device of claim 12, wherein a removable impermeable barrier covers the dispersion opening.

16. The dispensing device of claim 15, further including a support structure disposed within the second carrier to provide support to the second carrier.

17. The dispensing device of claim 16, wherein the support structure is selected from the group consisting of: a grid, a perforated plate, or a peripheral collar.

* * * * *